United States Patent [19]
Cassaday et al.

[11] Patent Number: 5,237,853
[45] Date of Patent: Aug. 24, 1993

[54] METHOD AND APPARATUS FOR MEASURING THE DENSITY OF A LIQUID

[75] Inventors: Ernest W. Cassaday, Apache Junction; James S. Roundy, Gilbert, both of Ariz.

[73] Assignee: AlliedSignal Inc., Morris Township, Morris County, N.J.

[21] Appl. No.: 944,816

[22] Filed: Sep. 14, 1992

Related U.S. Application Data

[63] Continuation of Ser. No. 597,945, Oct. 15, 1990, abandoned.

[51] Int. Cl.$^5$ .............................................. G01N 9/00
[52] U.S. Cl. .................................... 73/32 A; 73/19.03
[58] Field of Search ............... 73/19.03, 19.04, 32 A, 73/861.02, 861.19

[56] References Cited

U.S. PATENT DOCUMENTS

| | | | |
|---|---|---|---|
| 4,050,304 | 9/1977 | Thomas | 73/861.19 |
| 4,175,423 | 11/1979 | Braun et al. | |
| 4,508,127 | 4/1985 | Thurston | 73/861.02 |
| 4,644,781 | 2/1987 | Mon | 73/861.19 |

FOREIGN PATENT DOCUMENTS 0117150 8/1984 European Pat. Off. .

*Primary Examiner*—John E. Chapman
*Attorney, Agent, or Firm*—Joseph R. Black; James W. McFarland; Robert A. Walsh

[57] ABSTRACT

A process for monitoring fluid density by use of a fluidic jet oscillator (26) absent the necessity for a high-precision pressure regulator. Fluid is delivered to the fluidic oscillator (26) via a pressure divider (28). As the fluid flows through the oscillator the latter generates a pressure wavetrain at a frequency which is indicative of the density of the fluid, but is inaccurate to the extent that the pressure difference across the oscillator varies from a predetermined value. A differential pressure transducer (30) senses the pressure difference. Accordingly, the process is adapted for use with a gated sampling and control system (84) which operatively responds to the oscillator output only when the differential pressure is substantially in accord with a predetermined value thereof.

6 Claims, 3 Drawing Sheets

METHOD AND APPARATUS FOR MEASURING THE DENSITY OF A LIQUID

This is a continuation of application Ser. No. 07/597,945, filed Oct. 15, 1990, now abandoned.

The disclosure of U.S. Pat. Nos. 4,508,127 Thurston and 4,930,357 Thurston et al is incorporated herein by reference thereto.

TECHNICAL FIELD

This invention relates generally to liquid density measurement, and more specifically to liquid density measurement by electrofluidic means.

BACKGROUND OF THE INVENTION

In a fluidic oscillator the oscillation frequency of the fluid jet is directly dependent on the velocity of the fluid in the jet stream. If the differential pressure across the oscillator is held constant, then the density of the fluid is directly proportional to a constant divided by the square of the oscillation frequency. Such oscillators are disclosed in the above-referenced patents.

When employed as density sensors these oscillators are combined with pressure regulators (such as the regulator 42 illustrated in FIG. 2 of the '127 patent) to provide the constant differential pressure that is required. However, the pressure regulators are relatively massive, accounting for over ninety percent of the weight of the density meter. This creates problems in applications such as aircraft, for example, where weight and volume considerations may determine the choice made from among various density metering schemes.

An objective of this invention is to provide a process for electrofluidic liquid density measurement that accommodates the condition of varying differential pressure across the oscillator.

A further objective is to provide relatively lightweight and low-volume apparatus adapted for use with the above-mentioned process.

SUMMARY OF THE INVENTION

This invention achieves the forementioned objectives by enabling the use of a fluidic jet oscillator as a density meter absent the requirement for a conventional high-precision pressure regulator.

In monitoring liquid density according to the invention, the liquid flows through a pressure divider and is forced under pressure through the fluidic oscillator. The oscillator responsively outputs a frequency signal that is indicative of the density of the liquid but is in error whenever the differential pressure across the oscillator varies from a predetermined value. The differential pressure is sensed by either two separate transducers or a single differential pressure transducer to produce a differential pressure signal.

Although the differential pressure will vary due to the substitution of a pressure divider for a precision pressure regulator, the frequency signals can be treated as spurious when the differential frequency signal is not in substantial accord with the predetermined value. Therefore, by employing the differential pressure signals as enabling signals in a gated control system which operatively responds to the frequency signals only when the differential pressure signals are substantially in accord with the predetermined value, one can accurately monitor the density of a liquid by use of a fluidic oscillator in combination with a pressure divider and a differential pressure transducer. The use of a mere pressure divider in conjunction with a differential pressure transducer as a substitute for a high-precision pressure regulator permits a weight reduction in excess of ninety percent.

DESCRIPTION OF THE PREFERRED EMBODIMENT

Figure 1:
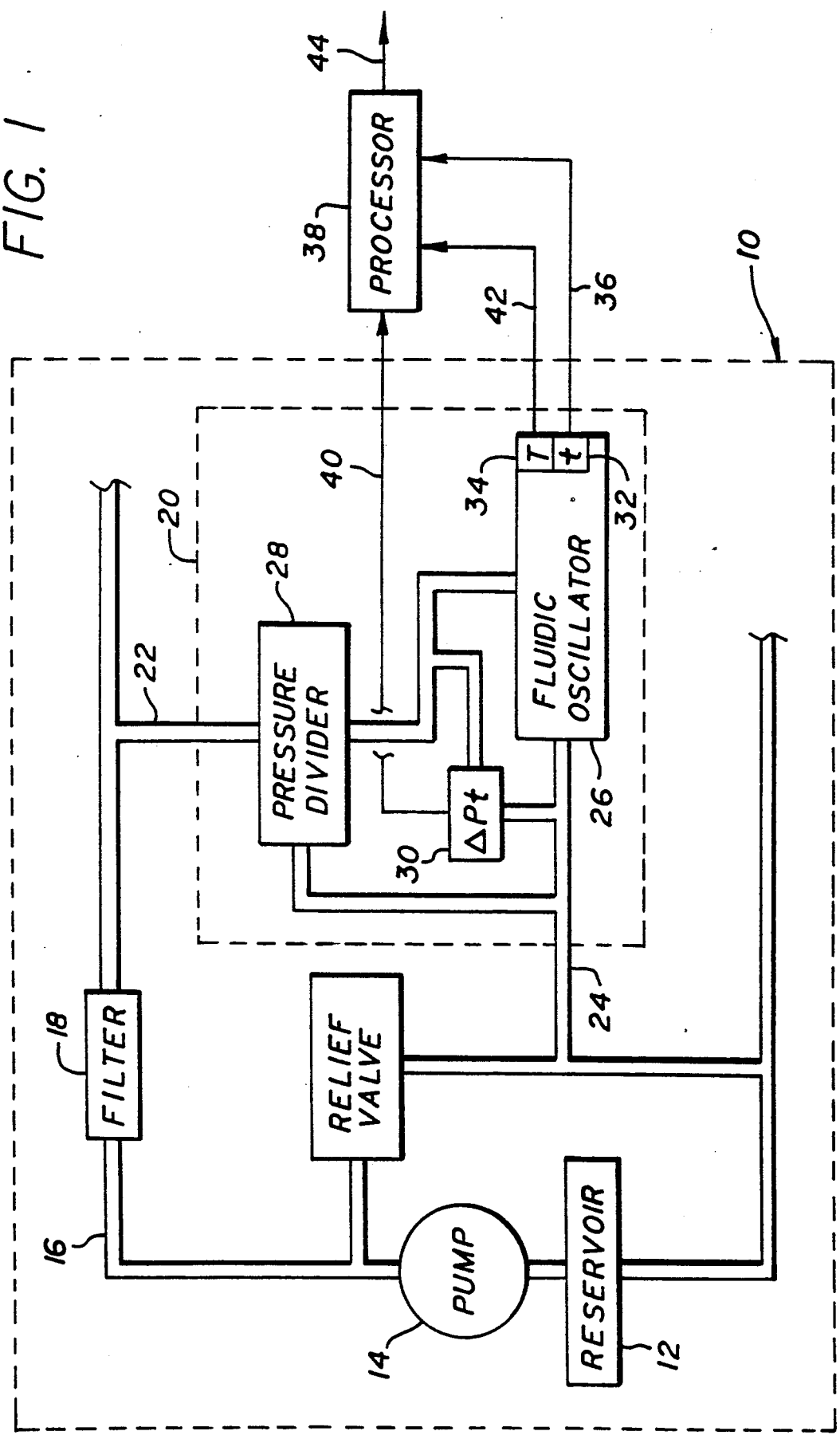
FIG. 1 is a schematic illustration of an aircraft hydraulic system incorporating the invention.

FIG. 1 is a schematic drawing partially illustrating an aircraft hydraulic system 10 which embodies principles of the present invention. Hydraulic oil from a reservoir 12 is supplied via a pump 14 along a main supply conduit 16 and through a high-pressure filter 18.

An air-in-oil sensor 20 receives the oil along a branch supply conduit 22 and returns the same to reservoir 12 via a branch vent conduit 24. The sensor 20 comprises a fluidic jet oscillator 26, a pressure divider 28, and a differential pressure transducer 30. The fluidic oscillator 26 is conventional in construction and is adapted to produce an output signal indicative of the density of the oil. The oscillator 26 is similar to apparatus described in the above-referenced patents, except that it is configured such that its two pressure transmission passages lead to opposite sides of a single piezoelectric transducer 32 rather than to separate transducers, and that it incorporates a thermistor 34 to monitor the temperature of the oil. Accordingly, the oscillator 26 in operation generates pressure pulsators that bear information indicative of the density of flowing therethrough. This information is, communicated via the transducer 32 as an electrical frequency signal along a wire 36 to an external electronic processor 38. The differential pressure transducer 30 and thermistor 34 are elements of external circuit branches (indicated by lines 40, 42) connected to the processor 38 to provide differential pressure and temperature signals thereto. The processor 38 operatively responds to the frequency signals (as by communicating a change in status along an output line 44) only when the differential pressure signals are substantially in accord with a predetermined amplitude or frequency.

Figure 3:
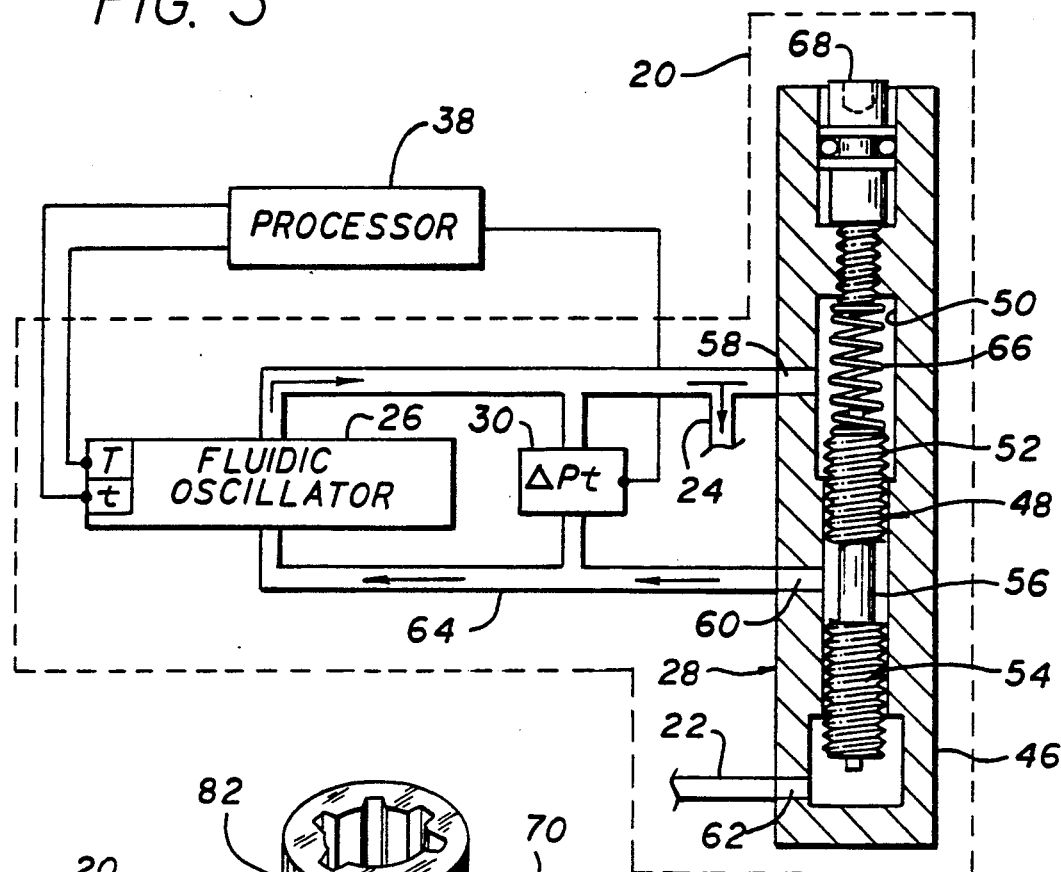
FIG. 3 is a generally schematic and partially cross-sectional illustration of the apparatus shown in FIG. 2.

The sensor 20 is further illustrated in FIG. 3 wherein the pressure divider 28 is shown in greater detail. The divider 28 is formed by a cylindrical housing 46 and a cylindrical spool 48. The housing 46 has an axially extending stepped bore 50 formed therein. As indicated, the spool 48 has two larger-diameter threaded end portions 52, 54 separated by a smaller-diameter center portion 56. The end portions 52, 54 cooperate with the inner surface of the housing 46 to define two spaced flow restrictors. Three cross-bores extending from the outer surface of the housing 46 to the stepped bore 50 provide ports 58, 60, 62 through which the pressure divider 28 is in fluid communication with the branch vent conduit 24, an intermediate supply passage 64 leading to the supply port of the oscillator 26, and the branch supply conduit 22, respectively. The spool 48 is slidably disposed in a smaller-diameter portion of the stepped bore 50 as indicated so that the center portion 56 straddles the center port 60. A biasing spring 66 is rigidly secured to an adjustment screw 68 which is threadedly engaged with the housing 46. There is no preload on the spring 66. Thus, the spool 48 is urged against the spring 66 in response to the oil which is received at supply pressure through the high-pressure port 62. The spring 66 provides limited pressure regulation during operation of the sensor 20.

Figure 2:
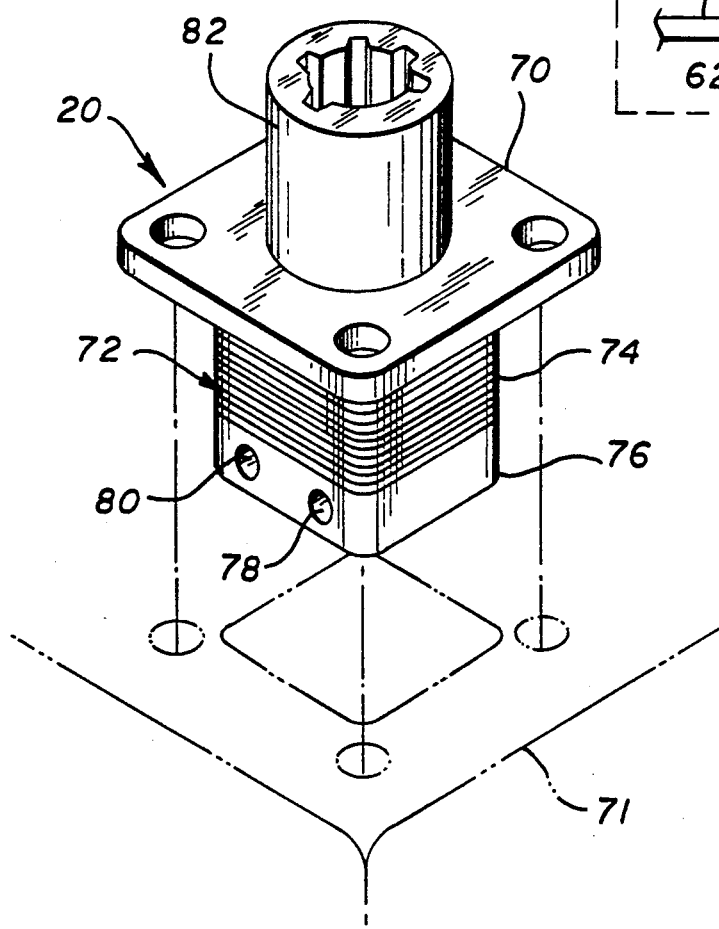
FIG. 2 is a perspective view of a contemplated electrofluidic circuit element adapted for use with the invention.

As currently contemplated, the sensor 20 is illustrated in FIG. 2. A mounting plate 70 is adapted for securement to a manifold 71 of the hydraulic system 10 (FIG. 1). Rigidly secured to one side of the plate 70 is a laminar structure 72 comprising a plurality of thin laminae 74 which collectively form the oscillator 26, and a thick base laminate or block 76. The base laminate 76 is adapted to receive the pressure divider 28 by the provision of a first-bore 78, and to receive the thermistor 34 and differential pressure transducer 30 by the provision of a second bore 80. The differential pressure transducer 30, thermistor 34, and pressure divider 28 are inserted in the indicated bores 78, 80 and rigidly secured within the structure 72 by suitable means so that the sensor 20 is formed as an integral electrofluidic circuit element. Accordingly, the laminar structure 72 is adapted by the provision of channels (not shown) therein to provide for the required fluid communication indicated by FIGS. 1 and 2. Likewise, both the laminar structure 72 and mounting plate 70 are adapted to provide for electrical communication from the differential pressure transducer 30 and thermistor 34 to a cylindrical boss 82 which is rigidly secured to the mounting plate 70 and is adapted for electrical connection to the processor 38 (FIG. 1).

In operation, high-pressure oil is supplied from the branch supply conduit 22 to the high-pressure port 62 of the pressure divider 28. The oil pressure is stepped down by the pressure divider 28 and a portion of the oil flows at a lower pressure through the center port 60, along the supply passage 64, and to the supply port of the oscillator 26. As the oil flows through the oscillator 26 to the vent passage 24, the oscillator generates a fluidic wavetrain having a frequency which depends on the density of the oil and on the difference in pressure between the supply passage 64 and the vent passage 24. The fluidic frequency signals are transduced to electrical frequency signals which are communicated to the processor 38. The differential pressure transducer 30 is fluidically connected across the oscillator 26 as indicated in FIG. 3, and is electrically connected to the processor 38 so as to function as a differential-pressure-responsive oscillator. Accordingly, depending on the selected circuit configuration, the differential pressure transducer 30 provides amplitude or frequency signals which vary with the pressure difference between the supply and vent passages 64, 24. These signals are communicated to the processor 38, and the latter incorporates any of a variety of circuits which employ the signals received from the differential pressure transducer 30 to enable an operative control response only when the amplitude or frequency of the signal is in substantial accord with that associated with a predetermined differential pressure.

Figure 4:
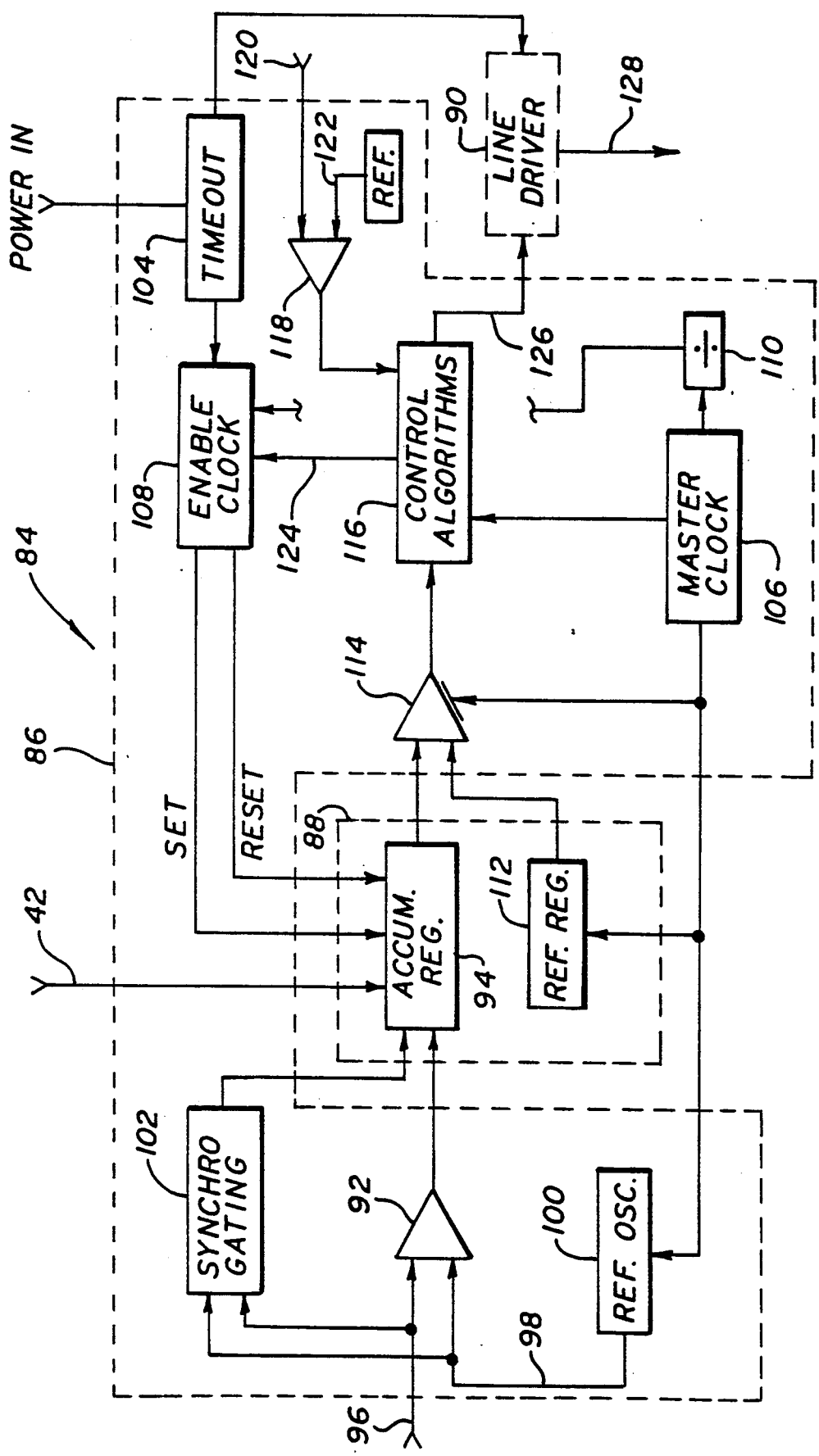
FIG. 4 is a schematic illustration of a gated electronic control system adapted for use with the invention.

FIG. 4 illustrates an exemplary gated sampling and control system 84. The system 84 is embodied in integrated circuit chips incorporating CMOS chip architecture and comprising a microprocessor 86, a memory register 88, and a current limiting line driver 90.

A buffer amplifier 92 and accumulator register 94 form a differential counting register that receives frequency inputs 96, 98 from the fluidic oscillator 26 and a reference oscillator 100. The reference oscillator 100 is adapted to provide a predetermined reference frequency equivalent to that which is outputted by the fluidic oscillator 26 when the latter is operated at the predetermined differential pressure with zero percent air content in the oil. To provide initial noise immunity, the differential frequencies are synchrogated into the accumulator register 94 on a continuous basis. The accumulator register 94 receives the differential frequency count, and receives the temperature signal from the thermistor 34. The latter signal is employed in the accumulator register 94 to bias the least significant bit and compensate for frequency shift due to temperature differences between the reference oscillator 100 and the fluidic oscillator 26. The synchrogating circuit 102 is adapted to gate only those frequencies that accurately represent air content over the range of air content for which the system is designed. To prevent anomalies during start-up, a time-out circuit 104 inhibits operation of the system 84 for a period of time prescribed by the user to enable the hydraulic system 10 (FIG. 1) to achieve stability of flow and air content. After that period, the system 84 is brought on line and the master clock 106 starts the microprocessor 86. An enable clock 108 is provided from the output of the master clock 106 via a frequency divider 110. The enable clock 108 sets a sampling period for the accumulator register 94 and resets the register at the end of the period. Prior to reset, the data count of the accumulator register 94 is compared with a reference count from a reference register 112 by clocking both into a digital comparator 114. The output from the reference register 112 is a count limit associated with the frequency output from the fluidic oscillator 26 when the latter is operated at the predetermined differential pressure and with oil having a maximum percentage of air content as prescribed by the user. The output of the comparator 114 is an input to a set of control algorithms 116 programmed into the microprocessor 86. The digital output of a second comparator 118 is an input to the same set of algorithms. The inputs to the second comparator 118 are a voltage signal 120 received from the differential pressure transducer 30, and a reference voltage level 122 corresponding to the amplitude of the voltage signal 120 at the predetermined differential pressure. When the input 120 is substantially in accord with the input 122, the output of the second comparator enables the microprocessor 86 to communicate a sampling command 124 to the enable clock 108. The control algorithms 116 incorporate a conventional seven-sample retry system to validate data which indicate excessive air content. When the accumulator register 94 and reference register 112 counts are sufficiently different to indicate by the output of the first comparator 114 that air content is excessive, seven sampling periods are used to validate the data. If any of the seven sampling periods does not yield a consistent output from the comparator 114, the data are rejected as invalid. If all seven sampling periods show consistency in the output, a command signal 126 is communicated to the line driver 90, which operatively responds to the command signal by communicating to a cockpit display or vehicle management system a signal 128 indicating a change in status. Preferably, an additional algorithm is employed to detect a slowly changing air content that may cause the accumulator register 94 to contain a residual count over a seventy-unit sampling period. If seventy sampling periods register a consistently detectable count accumulation exceeding the count of the reference register 112, the microprocessor 86 communicates the command signal 126 to the line driver 90.

The foregoing portion of the description, which description includes the accompanying drawings, is not intended to restrict the scope of the invention to the preferred embodiment thereof or to specific details which are ancillary to the teaching contained herein. The invention should be construed in the broadest manner consistent with the following claims and their equivalents.

What is claimed is:

1. Apparatus for the use in monitoring liquid density, comprising:
    a fluidic oscillator adapted to produce output signals indicative of the density of a liquid flowing therethrough;
    means connected across the oscillator for sensing differential pressure; and
    a pressure divider adapted to receive pressurized fluid from a source thereof, the pressure divider comprising a housing member having a stepped cylindrical bore formed therein; and a spool member slidably disposed in the bore and cooperating with the housing member to form first and second flow restrictors; the housing and spool members being cooperable in response to pressure variations to vary flow restriction by the first and second flow restrictors;
    the oscillator, pressure sensing means, and pressure divider being interconnected so as to cooperatively form an integral electrofluidic circuit element defining first, second, and third pressure levels of successively lower pressure; the oscillator, pressure sensing means, and second flow restrictor forming a parallel combination between the second and third pressure levels; and the first flow restrictor being interposed between the first and second pressure levels.

2. Apparatus for use in monitoring liquid density, comprising:
    a fluidic oscillator adapted to produce output signals indicative of the density of a liquid flowing therethrough;
    means connected across the oscillator for sensing differential pressure; and
    a pressure divider adapted to receive pressurized fluid from a source thereof, the pressure divider comprising first and second flow restrictors;
    the oscillator, pressure sensing means, and pressure divider being interconnected so a to cooperatively form an integral electrofluidic circuit element defining first, second, and third pressure levels of successively lower pressure; the oscillator, pressure sensing means, and second flow restrictor forming a parallel combination between the second and third pressure levels; the first flow restrictor being interposed between the first and second pressure levels;
    wherein the pressure divider further comprises means for forming a cylindrical bore, and a piston disposed in the bore so as to be slidable in axial directions, the piston having a threaded, radially outer surface along two spaced portions of its axial length, the piston having a larger diameter along the two spaced portions and a smaller diameter therebetween, the two spaced portions cooperating with the forming means to form the first and second flow restrictors.

3. The invention of claim 2 wherein the pressure divider further comprises means for biasing axially directed movement of the piston against liquid pressure at the first pressure level.

4. Apparatus for use in monitoring liquid density comprising:
    a fluidic oscillator adapted to produce output signals indicative of the density of a liquid flowing therethrough;
    means connected across the oscillator for sensing differential pressure, the sensing means being adapted to provide output data indicative of the differential pressure;
    a pressure divider adapted to receive pressurized fluid from a source thereof, the pressure divider comprising means for forming a cylindrical bore, and a piston disposed in the bore so as to be slidable in axial directions, the piston having a threaded, radially outer surface along two spaced portions of its axial length, the piston having a larger diameter along the two spaced portions and a smaller diameter therebetween, the two spaced portions cooperating with the forming means to form first and second flow restrictors;
    the oscillator, sensing means, and pressure divider being interconnected so as to cooperatively form an integral electrofluidic circuit element forming a fluidic circuit which includes the cylindrical bore and defining first, second, and third pressure levels of successively lower pressure; the oscillator, sensing means, and second flow restrictor forming a parallel combination between the second and third pressure levels; and the first flow restrictor being interposed between the first and second pressure levels; and
    electronic gating means, responsive to receipt of a reference datum and the output data, for operatively responding to the output data only when the data have magnitudes which are substantially equal to the reference datum.

5. The invention of claim 4 wherein the pressure divider further comprises means for biasing axially directed movement of the piston against liquid pressure at the first pressure level.

6. The invention of claim 1 wherein the pressure divider further comprises adjustable biasing means for varying the degree to which the flow restriction is varied in response to the pressure variations.

* * * * *